(12) United States Patent
Wachernig et al.

(10) Patent No.: US 7,884,932 B2
(45) Date of Patent: Feb. 8, 2011

(54) MEASURING INSTRUMENT

(75) Inventors: Hanno Wachernig, Diessen (DE); Achim Hogg, Diessen (DE)

(73) Assignee: Hanno Wachernig, Diessen (DE)

( * ) Notice: Subject to any disclaimer, the term of this patent is extended or adjusted under 35 U.S.C. 154(b) by 259 days.

(21) Appl. No.: 12/301,834

(22) PCT Filed: May 21, 2007

(86) PCT No.: PCT/EP2007/004496
§ 371 (c)(1), (2), (4) Date: Nov. 21, 2008

(87) PCT Pub. No.: WO2007/137724
PCT Pub. Date: Dec. 6, 2007

(65) Prior Publication Data
US 2010/0128266 A1    May 27, 2010

(51) Int. Cl.
*G01N 15/02* (2006.01)
(52) U.S. Cl. .................................................... 356/335
(58) Field of Classification Search .................. 356/335
See application file for complete search history.

(56) References Cited

U.S. PATENT DOCUMENTS

| 4,791,461 | A | * | 12/1988 | Kishimoto et al. | .......... 356/446 |
|---|---|---|---|---|---|
| 6,069,694 | A | * | 5/2000 | VonBargen | .................. 356/246 |
| 6,717,665 | B2 | * | 4/2004 | Wagner et al. | .............. 356/244 |
| 7,518,720 | B2 | * | 4/2009 | Kolp et al. | .................. 356/246 |
| 2007/0064226 | A1 | * | 3/2007 | Kolp et al. | .................. 356/246 |

FOREIGN PATENT DOCUMENTS

| CH | 396445 | 7/1965 |
|---|---|---|
| DE | 2032150 | 1/1972 |
| DE | 2808229 | 8/1979 |
| DE | 3516529 | 11/1986 |
| DE | 3828618 | 3/1989 |
| DE | 8907526.9 | 10/1989 |
| EP | 0075605 | 4/1983 |
| GB | 2097548 | 11/1982 |
| JP | 2000162118 | 6/2000 |

* cited by examiner

*Primary Examiner*—Roy Punnoose
(74) *Attorney, Agent, or Firm*—Volpe and Koenig, P.C.

(57) ABSTRACT

With a measuring instrument for measuring sample particles moving in a cuvette, for example for measuring a zeta potential or the Brownian size the particles, with a filling device for filling and an emptying device for emptying the cuvette mounted on the ends thereof and with devices for irradiating and for monitoring the particles, it is problematical always to position the cuvette correctly or in a defined manner relative to the direction of radiation and to the monitoring device. To resolve this problem, it is proposed that the cuvette member is mounted by means of a cuvette bearing and the filling and the emptying device are fastened exclusively to the cuvette in such a way that the position of the cuvette relative to the surroundings thereof is determined and defined exclusively by the cuvette bearing.

11 Claims, 2 Drawing Sheets

MEASURING INSTRUMENT

BACKGROUND

The invention relates to a measuring instrument according to the preamble to claim 1, in particular a measuring instrument for measuring sample particles moving in a cuvette, for example for measuring their speed and, derived therefrom, their electrophoretic mobility, zeta potential and Brownian particle size, with a filling device for filling and an emptying device for emptying the cuvette, which are mounted at the ends thereof and with devices for irradiating and for monitoring the particles.

The following describes an example of use of a measuring instrument of this kind, wherein it is expressly stressed that the invention does not refer solely to this example of use.

Colloids, emulsions or solid suspensions and mixtures have to be kept stable and homogeneous for the longest possible time. The formulations for these are becoming increasingly complex as the requirements increase. One of the possible methods for stabilising dispersed materials is to optimise electrostatic repulsion between particles of the same type in order to prevent the coagulation of these particles. Another set of problems of interest in this context relates to the targeted destabilisation, and hence separation, of dispersed materials in order to recover the water from the dispersion for the circuit. A large proportion of the measures for separating dispersed materials also involves particle charging, only in this case the charge is brought to zero if possible. However, in all cases it is necessary to know the charge ratios in order to be able to control them. The zeta potential reflects this charge. This can be measured by using a traditional method: microelectrophoresis.

During electrophoresis, electrically charged particles in a suspension or emulsion in an electrophoresis cell in the form of a cuvette are irradiated by means of a laser and by means of a microscope. The images recorded with the microscope are evaluated in order to determine the speed of the particles. The speed of the particles in the electric field is namely a measure for the electric charge whose potential can be depicted as the zeta potential and measured.

A significant problem with measurements of this kind is the exact positioning of the measuring setup or the parts thereof (laser-microscope-cuvette) relative to each other. It is also necessary for the cuvette to be both easy to fill and to clean.

SUMMARY

The invention is based on the object of disclosing a measuring instrument of the type described in the introduction in such a way that simple filling and ease of cleaning is facilitated, wherein simultaneously the measuring accuracy should remain very high.

This object is achieved by a measuring instrument according to claim 1.

In particular, the objective is achieved by a measuring instrument of the type described in the introduction in which the cuvette member is mounted by means of a cuvette bearing, wherein the filling and the emptying devices are fastened exclusively to the cuvette in such a way that the position of the cuvette relative to the surroundings thereof is determined or defined exclusively by the cuvette bearing.

Therefore, an essential point of the invention consists in the fact that the generally large and also heavy devices for filling and emptying the cuvette have no influence on the positioning of the actual cuvette. The cuvette is therefore so-to-speak used as a bearing element (contrary to its actual intended function).

Preferably, the filling and/or the emptying devices are fastened detachably to the cuvette for which a fastening device is used. This makes the cuvette easy to clean. This is then particularly simple if the fastening device comprises a quick release lock, in particular a bayonet lock. This also makes it possible to work without tools.

If electrodes are provided (as in the example described above), they can be attached at different points. Preferably, the electrodes are attached to the filling and/or to the emptying device for contact with the sample so that the cuvette can be embodied free of all parts which are disruptive during cleaning.

In a preferred embodiment, the cuvette bearing comprises two force-absorbing partial bearings extending at an angle—in particular a 90° angle—to a longitudinal axis leading through the cuvette. In particular, these can be a vertical partial bearing and a horizontal partial bearing. These partial bearings are preferably embodied as point bearings, which enables particularly precise adjustment. These point bearings can be produced particularly simply and precisely by bearing balls or bearing tips.

One of the two partial bearings comprises three bearing points defining a plane and supports a surface of the cuvette. The other partial bearing comprises two bearing points defining a straight line, wherein this straight line does not extend perpendicularly to the longitudinal axis of the cuvette. Preferably, the straight line extends parallel to this longitudinal axis. These two bearing points hold the surface adjacent to the aforementioned first surface of the cuvette in a defined way. The 5-point bearing formed in this way ensures a statically determined bearing perpendicular to the longitudinal axis of the cuvette. This provides a faultless and reproducibly defined bearing of the cuvette relative to the surroundings thereof that is in particular relative to a laser source and a monitoring microscope.

The device for irradiating (the laser) and the device for monitoring (the microscope) are connected directly or indirectly to each other together with the cuvette bearing for the definition of the positions relative to each other. This makes it possible to repeatedly perform reproducible measurements following the removal and re-installation of the cuvette in the instrument without any further subsequent adjustment.

BRIEF DESCRIPTION OF THE DRAWINGS

The following describes an example of an embodiment of the invention in more detail with reference to drawings, which show FIG. 1 a schematic exploded view of a cuvette with bearing FIG. 2 a section along the plane II-II in FIG. 1

DETAILED DESCRIPTION OF THE PREFERRED EMBODIMENT

In the following description, the same reference numbers are used for identical parts and parts with an identical function.

Figure 1:
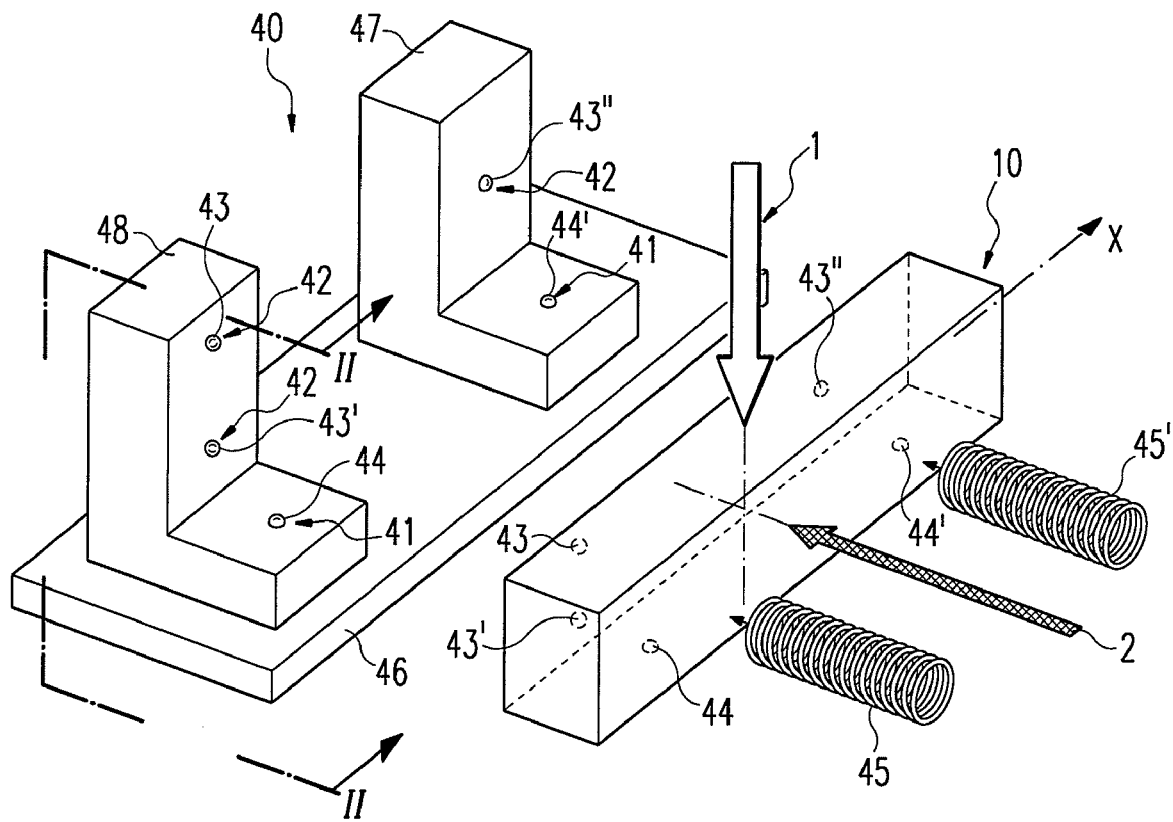

In FIG. 1 there is a schematic diagram of a cuvette 10 through the upper top surface of which an irradiating device 1 sends a laser beam into the interior of the cuvette, while a monitoring device 2 "looks" through the front face perpendicular to the upper surface into the interior of the cuvette. The focussing is such that the foci meet in a predetermined point in the cuvette.

Provided to bear the cuvette 10 is a cuvette bearing 40, which comprises holders 47, 48 fastened to a base plate 46 which are shown as angular here. In FIG. 1 the front holder 48 comprises on its vertical surface two bearing balls 43, 43' and on its horizontal surface a bearing ball 44. The other, in FIG. 1 rear holder 47 comprises on its vertical surface a bearing ball 43" and on its horizontal surface a bearing ball 44'. In FIG. 1, the arrangement of the bearing balls 43, 44 is also shown on the cuvette 10 (with dotted lines). Therefore, the bearing balls 43, 43' and 43" form a horizontal bearing 42, which holds the cuvette 10 in the horizontal direction against the pressure force of springs 45, 45', which press the cuvette 10 in the horizontal direction on the bearing balls 43, 43', 43".

Figure 2:
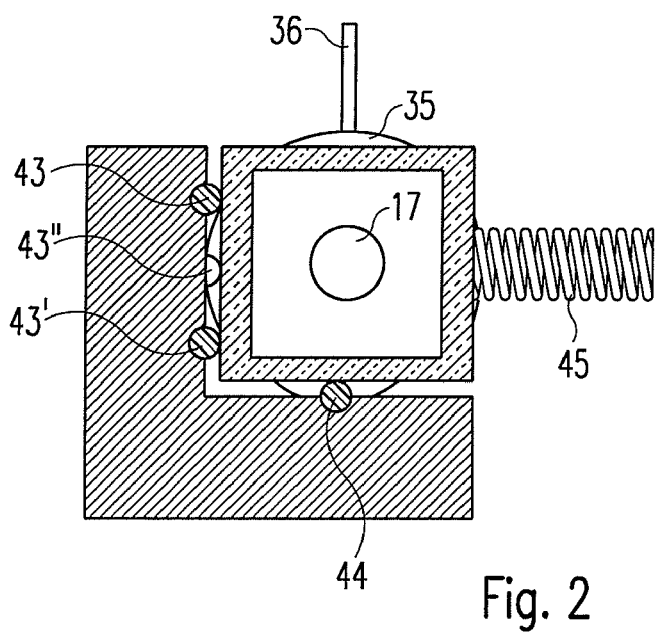

The weight, that is the vertical forces, is intercepted by the balls 44, 44' forming a vertical partial bearing 41. This causes the position of the cuvette 10 to be clearly defined as far as its position in its longitudinal axis X. The position in the X axis in turn plays no role with reference to the irradiating device 1 and the monitoring device 2 so that here no defined position has to remain secured. The relationships in assembled condition are shown again in FIG. 2. In addition, the cuvette is preferably pressed by a spring onto the vertical partial bearing 41.

According to FIG. 3-FIG. 6, the cuvette 10 comprises a member 11 which is constructed in a way known per se from plane-parallel plates. Flanges 12 and 13 are firmly attached to the ends of the cuvette 10, preferably sintered on with a glass body. Provided on the flanges 12 and 13 or on the conduction blocks 25, 35 are grooves for seals 14, 15 which can be embodied as O-rings. Located in the flanges 12, 13 are openings 16, 17 so that the cuvette 10 is open at both sides.

Figure 3:
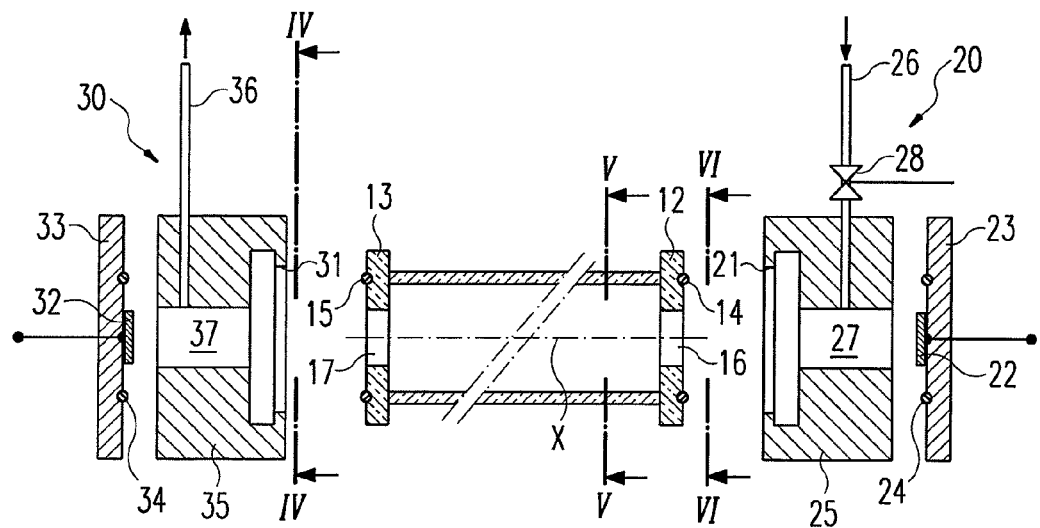
FIG. 3 a schematic exploded view of the cuvette with filling and emptying device in longitudinal section FIG. 4 a view along the line IV-IV in FIG. 3
Figure 4:
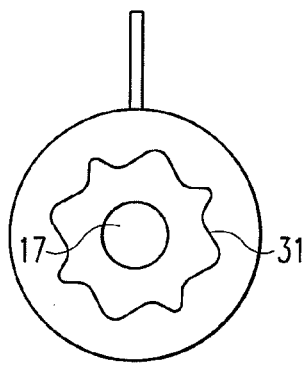
Figure 5:
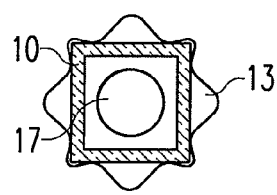
FIG. 5 a section along the line V-V in FIG. 3
Figure 6:
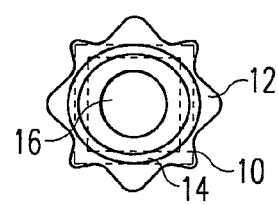
FIG. 6 a view along the line VI-VI in FIG. 3.

A filling device 20 can be positioned at the right-hand side in FIG. 3 and an emptying device 30 at the left-hand side in FIG. 3. For this, the flanges 12, 13 are embodied asymmetrically to their centre axis as is evident in particular from FIGS. 5 and 6. The filling device 20 and the emptying device 30 comprise fasting rings 21 or 31 whose openings are embodied to correspond to the periphery of the flanges 12, 13. Therefore, the filling device and the emptying device 30 can be placed on the lid 12, 13 as with a bayonet lock and skewed with respect to the cuvette 10 so that the filling device 20 and the emptying device 30 are firmly connected under compression of the seals 14, 15 to the lids 12, 13 and hence to the cuvette 10.

The filling device 20 and the emptying device 30 comprise a first conduction block 25 or a second conduction block 35 in each of which there are hollow spaces 27 or 37. These hollow spaces 27, 37 are sealed from the outside from the lid 23 or 33 which are fastened to the conduction blocks 25, 35 by seals 24 or 34 by means of (not shown here) connecting devices, for example screws.

Electrodes 22 or 32 are fastened to the lids 23, 33 in such a way that they protrude into the hollow spaces 27, 37 in assembled condition, wherein the electrodes 22, 32 are connected via lines leading outward to a voltage source for the generation of an electrophoretically active field.

Figure 7:
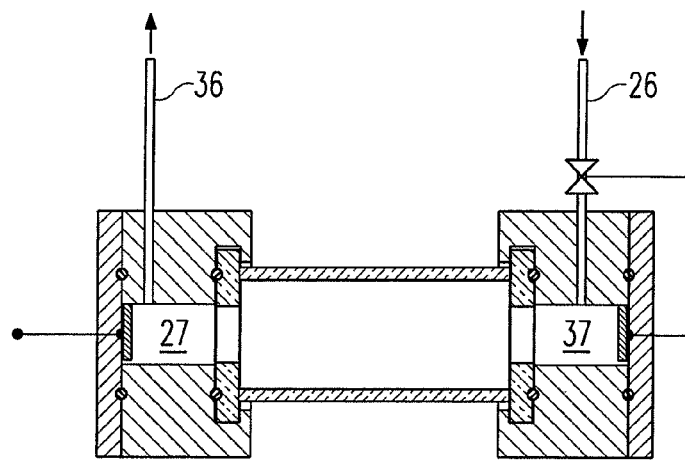
FIG. 7 the arrangement according to FIG. 3 in assembled condition in a sectional view

A supply lead 26 which can be shut-off by a valve 28 discharges into the hollow space 27 and a drainage line 36 discharges into the hollow space 37. As shown in FIG. 7, in assembled condition, the resulting hollow space can be filled with a sample fluid.

To clean the cuvette, the whole arrangement (as shown in FIG. 7) is removed from the cuvette bearing 40. Then, the filling device 20 and the emptying device 30 are removed by rotation in relation to the cuvette 10. The cuvette 10 can now be cleaned. Assembly is performed just as simply in the reverse way.

LIST OF REFERENCE NUMBERS

1 Irradiating device
2 Monitoring device
10 Cuvette
11 Member
12 Flange
13 Flange
14 Seal
15 Seal
16 Opening
17 Opening
20 Filling device
21 Fastening ring
22 Electrode
23 Lid
24 Seal
25 1st conduction block
26 Supply line
27 Hollow space
28 Valve
30 Emptying device
31 Fastening ring
32 Electrode
33 Lid
34 Seal
35 2nd conduction block
36 Drainage line
37 Hollow space
40 Cuvette bearing
41 Vertical partial bearing
42 Horizontal partial bearing
43, 43', 43" Bearing balls
44, 44' Bearing balls
45, 45' Pressure spring
46 Base plate
47 Holder
48 Holder

The invention claimed is:

1. Measuring instrument for measuring sample particles moving in a cuvette (10) to measure a zeta potential or the Brownian particle size of the particle, comprising a filling device (20) for filling and an emptying device (30) for emptying the cuvette (10), which are mounted on the ends thereof and with devices (1, 2) for irradiating and for monitoring the particles, the cuvette (10) member (11) is mounted by a cuvette bearing (40) and the filling device and the emptying device (20, 30) are fastened exclusively to the cuvette in such a way that a position of the cuvette (10) relative to the surroundings thereof is determined/defined exclusively by the cuvette bearing (40).

2. Measuring instrument according to claim 1, wherein at least one of the filling or the emptying device (20, 30) are fastened detachably to the cuvette (10) by a fastening device (21, 31).

3. Measuring instrument according to claim 2, wherein the fastening device (21, 31) comprises a quick release lock.

4. Measuring instrument according to claim 3, wherein the quick release lock is a bayonet lock.

5. Measuring instrument according to claim 1, wherein electrodes (22, 32) for contact with the sample are attached to the filling or emptying device (20, 30).

6. Measuring instrument according to claim 1, wherein the cuvette bearing (40) comprises two force-absorbing partial bearings (41, 42) extending at a 90° angle, to a longitudinal axis (X) leading through ends of the cuvette (10), comprising a vertical partial bearing (41) and a horizontal partial bearing (42).

7. Measuring instrument according to claim 6, wherein one of the partial bearings (42) comprises three bearing points defining a plane and the other partial bearing (41) comprises two bearing points defining a straight line, wherein the straight line extends not perpendicular to the longitudinal axis (X).

8. Measuring instrument according to claim 7, wherein the straight line extends parallel to the longitudinal axis (X).

9. Measuring instrument according to claim 1, wherein the partial bearings (41, 42) are embodied as point bearings.

10. Measuring instrument according to claim 9, wherein the point bearings comprise bearing balls (43, 44) or bearing tips.

11. Measuring instrument according to claim 1, wherein the devices for irradiating (1) and for monitoring (2) are connected directly or indirectly to each other with the cuvette bearing (40) to define their positions relative to each other.

* * * * *

UNITED STATES PATENT AND TRADEMARK OFFICE
CERTIFICATE OF CORRECTION

| | | |
|---|---|---|
| PATENT NO. | : 7,884,932 B2 | Page 1 of 1 |
| APPLICATION NO. | : 12/301834 | |
| DATED | : February 8, 2011 | |
| INVENTOR(S) | : Hanno Wachernig and Achim Högg et al. | |

It is certified that error appears in the above-identified patent and that said Letters Patent is hereby corrected as shown below:

On the Title Page

Please add the following to the title page:

Item (30) Foreign Application Priority Data

May 31, 2006  (DE) ..................... 10 2006 025 392.2
June 21, 2006  (DE) ..................... 10 2006 028 516.6

Signed and Sealed this
Twenty-eighth Day of February, 2012

David J. Kappos
*Director of the United States Patent and Trademark Office*